United States Patent [19]

Berky et al.

[11] 4,026,774
[45] May 31, 1977

[54] COULOMETRIC MEASURING METHOD

[75] Inventors: Dénes Berky; Tamás Damokos; Jenö Havas; Henrik Muller, all of Budapest, Hungary

[73] Assignee: Radelkis Elektrokemiai Muszergyarto Szovetkezet, Budapest, Hungary

[22] Filed: June 25, 1975

[21] Appl. No.: 590,133

[30] Foreign Application Priority Data

July 2, 1974 Hungary .................... RA 619

[52] U.S. Cl. ................................................ 204/1 T
[51] Int. Cl.$^2$ ........................................ G01N 27/42
[58] Field of Search .......... 204/195 T, 1 M; 324/29

[56] References Cited

UNITED STATES PATENTS

| 2,928,774 | 3/1960 | Leisey | 204/1 M |
|---|---|---|---|
| 3,226,313 | 12/1965 | Riseman | 204/195 G |
| 3,338,812 | 8/1967 | Dworak et al. | 204/195 T |
| 3,383,299 | 5/1968 | Arthur | 204/195 G |
| 3,551,109 | 12/1970 | Dahms | 204/195 T |

*Primary Examiner*—G. L. Kaplan
*Attorney, Agent, or Firm*—Young & Thompson

[57] ABSTRACT

The invention relates to coulometric measuring for the determination of the concentration and/or factor of acids or bases. A reference electrode and a measuring electrode sensitive to the activity of hydrogen ions of the indicator circuit and an anode and a cathode electrode of the generator circuit, are arranged in the measuring cell of the measuring apparatus. As a depolarizer and potential determining substance, the chloride, bromide or iodide of potassium, sodium, rubidium, cesium, calcium, strontium or barium is added in excess to the supporting electrolyte in the measuring cell.

Inaccuracy and instability brought about by the diffusion potentials arising at the diaphragms can thus be eliminated.

7 Claims, 4 Drawing Figures

COULOMETRIC MEASURING METHOD

The invention relates to coulometric measuring for the determination of the concentration and/or factor of acids and bases by providing in a measuring cell 1 a reference electrode 18 of the indicator circuit and a hydrogen ion activity-sensitive measuring electrode 16, further an anode electrode 21 and cathode electrode 19 of the generator circuit, the latter being equipped with a current generator 5 and the measuring circuit with a measuring amplifier 7 connected to display unit 12 and its input being connected to the measuring electrode 16.

In volumetric analysis, accurately standardized titrant solutions are required. However, as it is well known, these cannot be prepared by simple weighting-in, but their concentration has to be determined by titration: the titrant solutions have to be "standardized." Moreover, the factor of titrant solutions often varies as a function of time and accordingly the standardization procedure must be repeated from time to time. One of the most frequently used titration procedures is acidi-alkalimetry; the basis of such measurements is an acid solution of accurately known factor.

Coulometric titration procedures constitute an important variant of titration techniques. In such titrations, the analytical reagent (in our case, some sort of base) is prepared electrolytically, with the help of suitable generator electrodes. This technique possesses numerous advantages: preparation of the alkali solution, their standardization and re-standardization, storage of the reagent solutions so as to prevent access of atmospheric carbon dioxide, and delivering of the solutions are dispensed with, whereby the procedure is speeded up and simplified to a considerable degree.

However, in spite of the advantages mentioned in the above, it is a drawback of the technique that the electrolytic cell applied is rather complicated. The reagent is produced at the generator cathode whereas an amount of acid, equivalent to that of the base produced, is formed at the anode. In order to be able to use the base produced for a titration, the acid formed has to be withheld from the system. This may be accomplished by surrounding the generator anode by a diaphragm. However, this results in a number of drawbacks: the diaphragm necessitates that the dimensions of the cell be increased to a considerable degree; if the dimensions of the diaphragm are decreased, its electrical resistance is increased. If this increase in resistance is balanced by increasing the voltage of the current source, unwanted heat evolution may occur. Moreover, keeping the diaphragm clean is cumbersome, its adsorptive action may cause interferences.

Further difficulties are encountered in connection with the indicator electrodes serving for indication of the endpoint of the chemical reaction. In acid titrations, an electrode sensitive to changes in pH (glass-, antimony-etc. electrode) used as a measuring electrode and a reference electrode of the second kind (most frequently a calomel- or a silver-silver chloride half cell) are applied in the indicator circuit. The electrolyte solution securing the potential determining process of the reference electrode (most frequently a potassium chloride solution) is placed in a salt-bridge closed with a diaphragm. The difficulties detailed in the above also manifest themselves in connection with this diaphragm. Further difficulties are brought about by the diffusion potential arising at the liquid junction between the solution contained in the salt-bridge and the sample solution; this potential is poorly defined, is not reproducible and consequently it may interfere with the observation of the end-point of the reaction.

The appearance of the diffusion potential as an interfering signal causes insurmountable difficulties especially in the determination of the dissociation equilibrium constants and pH values of acids because in addition to the error in the end-point of the titration, mentioned in the foregoing, a diffusion potential, different from that produced in the buffer solutions used for standardization of the electrodes, is produced in acid solutions.

All these difficulties have contributed to the fact that coulometric acid determinations, in spite of their advantages detailed in the foregoing, are seldom used in practical analytical chemistry.

Procedures that eliminate one or the other of the above-mentioned difficulties are known. For example, the generator anode need not be separated by a diaphragm if a depolarizer compound is added to the electrolyte solution which reacts at the generator anode with the formation of a reaction product that is insoluble in the electrolyte or escapes from it in the form of a gas. According to another known procedure, the reference electrode comprising no salt bridge is dipped immediately into the electrolyte solution and the material bringing about the potential determining process is dissolved in the same electrolyte. By varying the concentration of said material and by extrapolating the measured potential values to zero concentration, the potential value free of diffusion potential can be calculated.

According to another known procedure aimed at elimination of the adverse effect of the diaphragm in the indicator circuit, two identical measuring electrodes, e.g. two antimony electrodes are connected to the indicator circuit and polarized with a low, constant current; the voltage appearing across said electrodes is used as the signal of the indicator circuit. However, this technique is burdened by the drawback that the information given by the shape of the titration curve is lost because changes in the pH value of the solution being titrated cannot be followed by this method.

Our aim is to eliminate the adverse effects brought about by the application of diaphragms in coulometric acidbase determinations.

The procedures described in the foregoing, complicated in themselves, could be utilized simultaneously only if it were possible to find, on the one hand, a depolarizer material and, on the other, a reference electrode potential determining material which mutually do not interfere with the functioning of each other. This solution would offer further advantages inasmuch as it would allow coulometric preparation of the standardizing buffer solutions directly in the electrolyte solution as well as standardization of the measuring electrodes without the appearance of a diffusion potential.

The present invention is based on the realization that all aims described in the foregoing can be realized and all the recited difficulties can be overcome if an electrochemical system is constructed in which a single substance acts as the anodic depolarizer and simultaneously as the reference potential determining substance of the indicator circuit as well. Mutual interference cannot be encountered in this case. According to the invention, a material soluble in the solvent applied and containing an anion which forms an insoluble precipitate with the ions of the metal of the generator anode in the solvent applied is used as such a material. As the reference electrode of the indicator circuit, one whose potential is determined by the depolarizer and reference potential determining material is used (e.g. in an aqueous solution, an electrolyte containing potassium bromide, silver generator anode and a silver-silver bromide electrode of the second kind). The generator cathode is preferably made of a noble metal, the measuring electrode of the indicator circuit is preferably a glass electrode. The depolarizer and reference potential determining material is used in such an excess that its concentration remains practically constant during the measurement.

In the solution of the task according to the present invention, in order to eliminate the adverse effects of the diffusion potential arising at the diaphragms used in apparatuses known up to now, a diaphragmless reference electrode (18) of the basic material silver, lead, mercury or thallium is arranged within the measuring cell in a space common with the measuring electrode 16, and the chloride, bromide or iodide of potassium, sodium, rubidium, cesium, calcium, strontium or barium is added in an excess to the supporting electrolyte placed in the measuring cell as a depolarizer and potential determining material. Preferably, the anode electrode 21 of the generator circuit is also made of a material corresponding to the reference electrode 18 and the reference electrode, the measuring electrode, the anode electrode and the cathode electrode are arranged in the measuring cell in the same compartment in the same solution. The measuring amplifier 7 is equipped with a zero point shifting reference circuit 8 which can be controlled over a potential range corresponding to 0 to 14 pH units. In a preferable arrangement of the coulometric measuring apparatus a comparator is connected to the output of the measuring amplifier, further a switch coupled to the comparator and connected to the circuit of the current generator and charge integrating measuring unit are included. The measuring electrode is preferably surrounded by the reference electrode. The reference electrode may also be a selective ion-sensitive electrode.

The measuring system according to the present invention also allows high-precision standardization of pH-measuring electrodes if a weak acid or acidic salt, having a dissociation constant lower than 10$^{-1}$, is also added to the supporting electrolyte. An amount of alkali neutralizing part of the acid added is generated, whereby a buffer system is produced whose pH-value is determined by the amount of charge conducted through the system; this pH-value can be calculated on the basis of Faraday's law and the Debye-Huckel theory to a high degree of accuracy.

The high-precision buffer solutions, prepared according to the aforesaid, can be used for convenient and fast standardization of the pH-meter if the electrical zero-point of the latter (that particular input potential value at which the output voltage of the amplifier is zero) is set to a value corresponding to the pH-value of the buffer solution in the case of the given electrode system. The standardization is carried out at that point, and thereupon, by conducting a further amount of charge through the system, a second buffer solution of different pH-value is prepared in the same solution. The pH-meter is standardized at the second pH-value, by adjusting in this second case the slope of the amplifier of the pH-meter. In this manner, high-precision standardization at two points, unaffected by the interfering action of diffusion potential can be carried out without the otherwise unavoidable, timeconsuming and cumbersome iteration.

Figure 1:
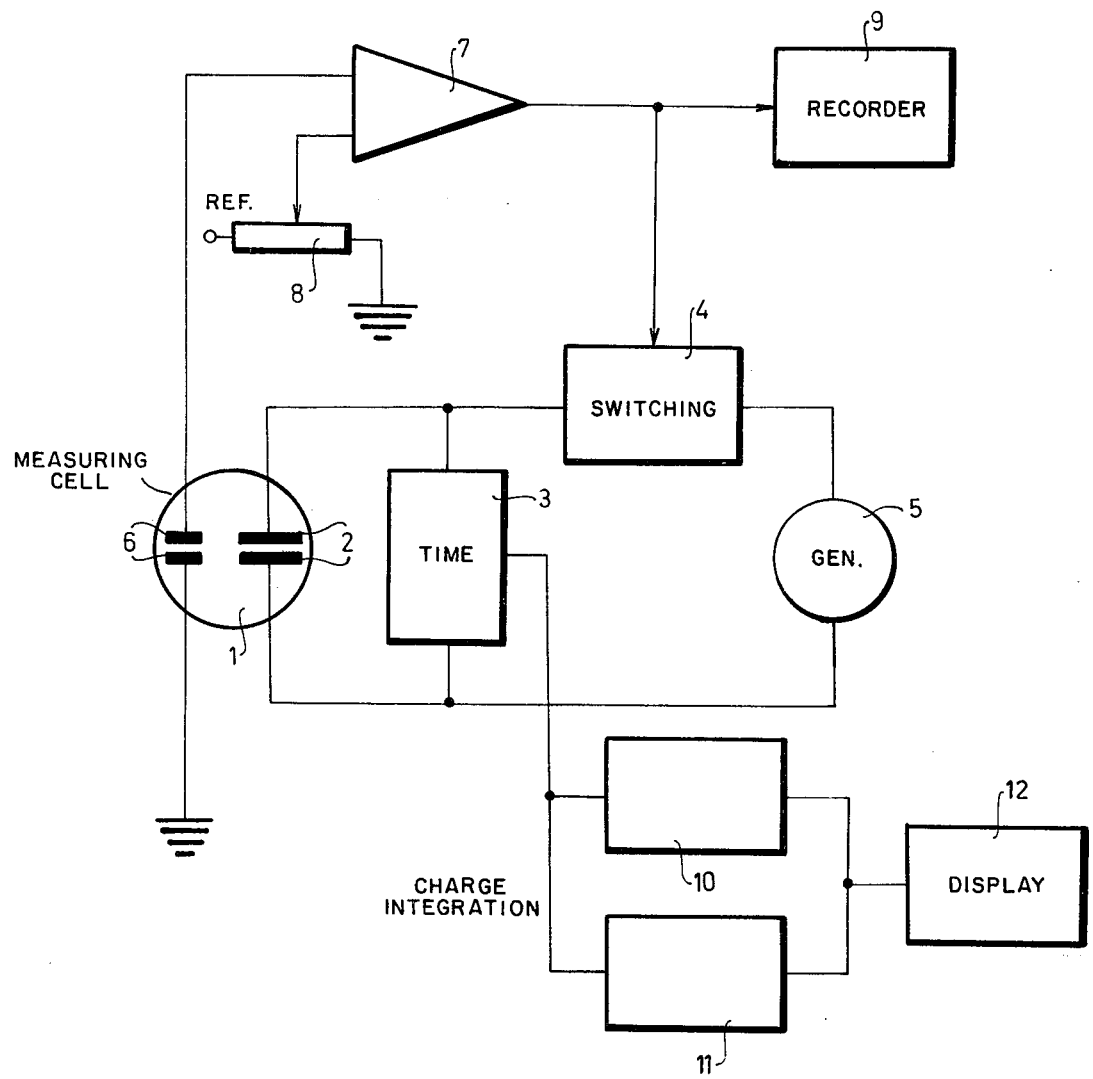
FIG. 1 is an example of the measuring apparatus suitable for the practice of the method according to the present invention.

An example of the measuring apparatus suitable for the practice of the method according to the present invention is presented in the block diagram of FIG. 1. The electrodes 2 connected to the generator circuit of measuring cell 1 are, on the one hand, connected to time measuring circuit 3, and, on the other, through switching and comparator circuit 4 to current generator 5. The potential appearing across the indicator electrodes 6 of the measuring cell is conducted to one input of measuring amplifier 7 whereas the other input is connected to a reference circuit 8.

The output of the differential amplifier embodying measuring amplifier 7 is connected to switching and comparator circuit 4 and to the input of recorder 9. The signal of time measuring circuit 3 is connected to display unit 12 through multiplying circuit 10 and/or reciprocal value computing unit 11; these circuits together constitute a charge integrating measuring unit.

Figure 2:
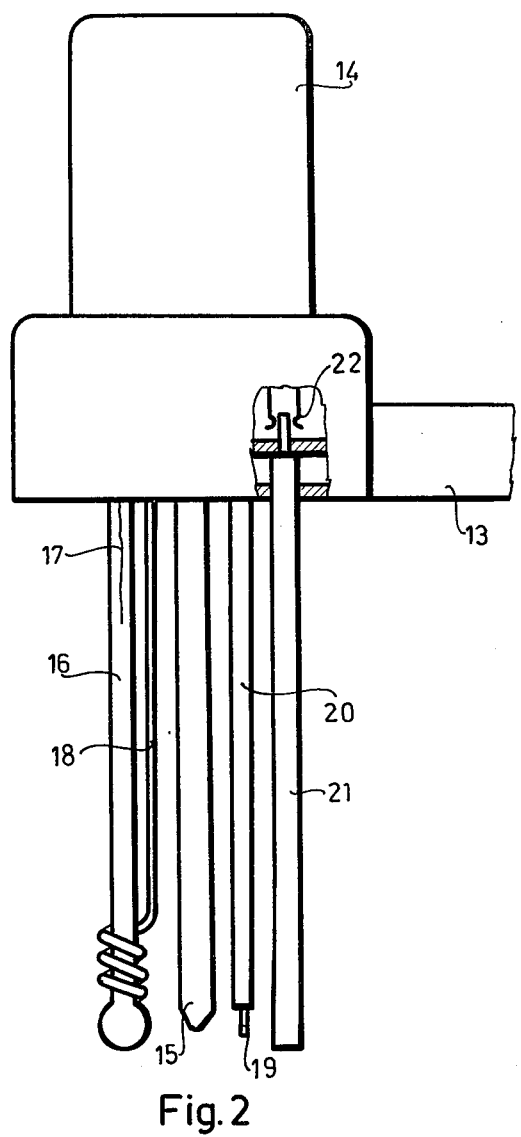
FIG. 2 depicts a measuring cell useable with the apparatus of FIG. 1.
Figure 3:
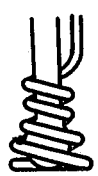
FIG. 3 depicts a typical arrangement of the glass and reference electrodes.

An example of the measuring cell used in conjunction with the measuring apparatus according to FIG. 1 is shown in FIG. 2. Supporting assemblage 13 holds stirring motor 14 which rotates stirrer rod 15. The sensing electrode 16 of the indicator circuit is a glass electrode; 17 is the internal lead of the latter. The reference electrode 18 of the indicator circuit is a silver spiral wire coated with a deposit of silver bromide. Even more preferably, reference electrode 18 is a selective ion-sensitive (in the case of the present example, a bromide-sensitive) electrode. In this case, potassium bromide is used preferably as depolarizing and potential determining compound. The cathode electrode 19 of the generator circuit is preferably a platinum or silver wire, whose shaft is — in order to decrease the scattering of the current lines — covered by an insulating sheathing 20. The generator anode is a silver wire 21 secured and, at the same time electrically contacted by a pair of springs 22. Arrangement of the generator electrodes in a radial plane decreases the scattering of the current lines and consequently this arrangement is preferably used. In order to further decrease the interaction between the indicator and generator circuits, reference electrode 18 may be produced in the form of a spiral (FIG. 3), or a wire net, perforated cylinder, etc. surrounding glass electrode 16.

Figure 4:
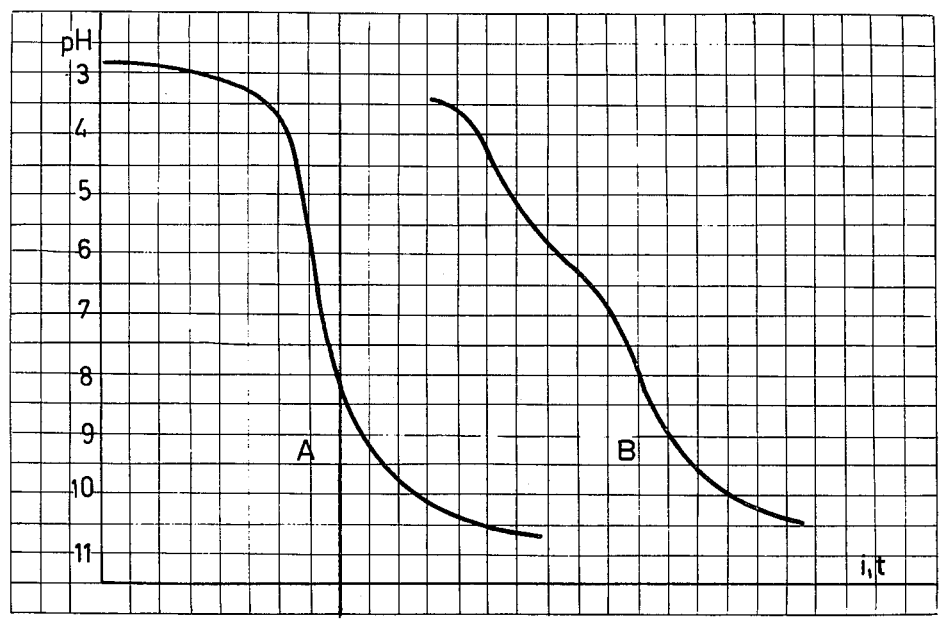
FIG. 4 is a graph showing two titration curves according to the invention.

In addition to potassium bromide, mentioned in the above example, the chloride, bromide or iodide of sodium, potassium, rubidium, cesium, calcium, strontium or barium can be used as depolarizer and potential determining substance, and in addition to silver mentioned in the above example, mercury, thallium or lead can be used as the material of the reference electrode of the indicator circuit. Two titration curves are presented as examples for the application of the measuring apparatus according to the present invention (FIG. 4). The supporting electrolyte when recording these curves was 5 ml of a potassium bromide solution of 0.5 M concentration; a glass and a silver-silver bromide electrode were used in the indicator circuit and silver electrodes in the generator circuit. The generator current was 26.8 mA. Curve A. shows the titration of 0.1 ml of a 0.1 M hydrochloric acid solution, curve B. that of 0.1 ml of a phosphate buffer solution of pH = 2. The two neutralization steps of phosphoric acid can be observed well separated in the latter curve.

What we claim is:

1. A coulometric measuring method for the determination of the concentration and/or factor of acids and bases, comprising establishing a measuring cell, an indicator circuit, and a generator circuit, immersing in a supporting electrolyte in said measuring cell (1) four electrodes comprising a reference electrode (18) of said indicator circuit, a hydrogen ion activity-sensitive measuring electrode (16), an anode electrode (21), and cathode electrode (19); passing an electrical current through said anode electrode and said cathode electrode via said generator circuit, the generator circuit being equipped with a current generator (5) and the measuring circuit with a measuring amplifier (7) connected to a display unit (9) and its input being connected to the measuring electrode (16); and overcoming the adverse effect of the diffusion potential brought about by the diaphragm applied in apparatuses known up to now, by providing the reference electrode (18) as a diaphragmless electrode of the basic material silver, lead, mercury or thallium within the measuring cell in a space common with the measuring electrode (16), and by adding the chloride, bromide or iodide of potassium, sodium, rubidium, cesium, calcium, strontium or barium to the supporting electrolyte in the measuring cell both as a depolarizer and as a potential determining material.

2. A coulometric measuring method, as described in claim 1, wherein the anode electrode (21) of the generator circuit is also made of a material corresponding to the reference electrode (18).

3. A coulometric measuring method, as described in claim 1, wherein the measuring amplifier (7) is equipped with a zero point shifting reference circuit (8) which can be controlled over a potential range corresponding to 0 to 14 pH units.

4. A coulometric measuring method, as described in claim 1, wherein a comparator connected to the output of the measuring amplifier, a switch coupled to the comparator and connected to the circuit of the current generator and a charge integrating measuring unit are included.

5. A coulometric measuring method, as described in claim 1, wherein the measuring electrode is surrounded by the reference electrode.

6. A coulometric measuring method, as described in claim 1, wherein the reference electrode is a selective ion-sensitive electrode.

7. A coulometric measuring method, as described in claim 1, wherein the supporting electrolyte also contains an acid or base or acidic salt of a dissociation equilibrium constant lower than $10^{-1}$ at a concentration of 0.0001 . . .4 moles/dm$^3$.

* * * * *